United States Patent [19]

Fahnestock et al.

[11] Patent Number: 4,828,994
[45] Date of Patent: May 9, 1989

[54] BACILLUS STRAINS WITH REDUCED EXTRACELLULAR PROTEASE LEVELS

[75] Inventors: Stephen R. Fahnestock, Olney; Kathryn E. Fisher, Bethesda, both of Md.

[73] Assignee: Genex Corporation, Gaithersburg, Md.

[21] Appl. No.: 733,379

[22] Filed: May 13, 1985

Related U.S. Application Data

[63] Continuation-in-part of Ser. No. 652,968, Sep. 21, 1984, abandoned.

[51] Int. Cl.$^4$ .................. C12N 1/20; C12N 15/00; C12P 21/00
[52] U.S. Cl. .................. 435/172.3; 435/68; 435/252.31; 435/320; 435/839; 935/10; 935/56; 935/42; 935/74
[58] Field of Search .................. 435/68, 172.1, 253, 435/172.3, 317, 839; 935/74, 42, 56, 10

[56] References Cited

U.S. PATENT DOCUMENTS 4,450,236 5/1984 Dean et al. .................. 935/58 X
4,617,266 10/1986 Fahnestock .................. 435/68

FOREIGN PATENT DOCUMENTS 0124374 7/1984 European Pat. Off. .
0130756 1/1985 European Pat. Off. .
WO84/00381 2/1984 World Int. Prop. O. .

OTHER PUBLICATIONS

Wells, J. A. et al *Nucleic Acids Res* 11(22): 7911–7925 1983.
Dobrzhanskaya, E. O. *Chem Abstr* 85:89870 1976.
Shortle, D. et al *Science* 271:371–373 1982.
Haldenwang, W. G. et al *J. Bacteriol* 142(1):90–98 1980.
Chemical Abstracts, *Abstract No.* 226660f 101:434 (1984).
Kawamura et al., *J. Bacteriol.* 160(1):422–444 (1984).
3–Biochem. Genetics, *Abstract No.* 18528n 102:155 (1985).
Yang et al., *J. Bacteriol.* 160(1): 15–21 (1985).
Niaudet et al., *Gene* 19: 277–284 (1982).
Chemical Abstracts, *Abstract No.* 155686a 98: 88 (1983).
Hofemeister et al., *Mol. Gen. Genet.* 189: 58–68 (1983).
K. Struhl, *Gene* 26: 231–242 (1983).

*Primary Examiner*—Thomas G. Wiseman
*Assistant Examiner*—Joan Ellis
*Attorney, Agent, or Firm*—Saidman, Sterne, Kessler & Goldstein

[57] ABSTRACT

Bacillus strains having reduced levels of extracellular protease are produced by replacing the native chromosomal DNA sequence comprising the gene for an extracellular protease, such as subtilisin, with a partially homologous DNA sequence having an inactivating DNA segment inserted therein. The strains are useful as hosts for the expression and secretion of heterologous polypeptides or proteins.

20 Claims, 5 Drawing Sheets

```
1    TTTCGACAGGAATTTGCCGGGACTCAGGAGCATTTAACCTAAAAAGCATGACGACATTTCAGCATAATGAACATTTACTCATGTCTATTTCGTTCTTTT

101  CTGTATGAAATAGTTATTCGAGTCTCTACGGAAATAGCGAGATGATATACCTAAATAGAGATAAATCATCTCAAAAAAATGGGTCTACTAAAAT
                                                                     . . . . . . .
201  ATTATTCCATCTATTACAATAAATTCACAGAATAGTCTTTTAAGTAAGCTCTACTCTGAATTTTTTAAAGGAGAGGGTAAAGA GTG AGA AGC AAA
                                                                                        fMet Arg Ser Lys
                                                                                             -106

295  AAA TTG TGG ATC AGC TTG TGG TTT GCG TTA ACG TTA ATC TTT ACG ATG GCG TTC AGC ATG TCT GCG CAG GCT
     Lys Leu Trp Ile Ser Leu Leu Phe Ala Leu Thr Leu Ile Phe Thr Met Ala Phe Ser Asn Met Ser Ala Gln Ala
                         100                        -90                                           -80

370  GCC GGA AAA AGC AGT ACA GAA AAG AAA TAC ATT GTC GGA TTT AAA CAG ACA ATG GCC ATG AGT AGT TCC GCC AAG
     Ala Gly Lys Ser Thr Glu Lys Lys Tyr Ile Val Gly Phe Lys Gln Thr Met Ala Met Ser Ser Ala Lys
             Pro-                  70                                                            -60

445  AAA AAG GAT GTT TCT GAA AAA GGT GGA AAG GTT CAA AAG CAA TTT AAG TAT GTT AAC GCG GCA GCA ACA
     Lys Lys Asp Val Ser Glu Val Ile Ser Glu Gly Lys Val Gln Lys Gln Phe Lys Tyr Val Asn Ala Ala Ala Thr
                 50                         -40                                                 -30

520  TTG GAT GAA AAA GCT GTA AAA GAA TTG GAA TTG AAA GAT CCG AGC GTT GCA TAT GTG GAA GAA GAT CAT GCA CAT
     Leu Asp Glu Lys Ala Val Lys Glu Leu Lys Lys Asp Pro Ser Val Ala Tyr Val Glu Glu Asp His Ile Ala His
                                -20                                                        -10

595  GAA TAT GCG CAA TCT GTT CCT TAT CCT GTT ATC GAC AGC GGA ATT TCT CAA ATT AAA GGG CCG GCT CTT CAC GGC
     Glu Tyr Ala Gln Ser Val Pro Tyr Pro Val Ile Asp Ser Gly Ile Ser Gln Ile Lys Ala Pro Ala Leu His Gly
         -1 │ 1  Mature                10                                                        20

670  TCT AAC GGA GTA AAA GTA GCT GTT ATC GAC AGC GGA ATT GAC TCT TCT CAT CCT CAT AGC TTA AAC GTC AGA GGC GCA
     Ser Asn Val Lys Val Ala Val Ile Asp Ser Gly Ile Asp Ser Ser His Pro Asp Leu Asn Val Arg Gly Gly Ala
                     30                                         40

745  AGC TTC GTA CCT TCT GAA ACA AAC CCA TAC CAG GAC GGT AGT TCT CAC GGT ACG GTA GCC GGT ACG ATT GCC
     Ser Phe Val Pro Ser Glu Thr Asn Pro Tyr Gln Asp Gly Ser Ser His Gly Thr His Val Ala Gly Thr Ile Ala
                     50                     (Pro Asn)          60                             70

820  GCT CTT AAT AAC TCA ATC GGT GTT CTG GGC GTA TTA GGC GTT CTG GTA CCA AGC GCA TCA TTA TAT GCA GTA AAA GTG CTT GAT TCA
     Ala Leu Asn Asn Ser Ile Gly Val Leu Gly Val Ala Pro Ser Ala Ser Leu Tyr Ala Val Lys Val Leu Asp Ser
                     80                             (Ser Ala) 90
```

```
 895  ACA GGA AGC GGC CAA TAT AGC TGG ATT ATT AAC GGC ATT GAG TGG GCC ATT TCC AAC AAT ATG GAT GTT ATC AAC
      Thr Gly Ser Gly Gln Tyr Ser Trp Ile Ile Asn Gly Ile Glu Trp Ala Ile Ser Asn Asn Met Asp Val Ile Asn
                             100                                110                                120

970  ATG AGC CTT GGC GGA CCT ACT GGT TCT ACA GCG GTT GAC GTT AAA GCC GTT TCC AGC GGT ATC GTC
      Met Ser Leu Gly Gly Pro Thr Gly Ser Thr Ala Val Asp Val Lys Ala Val Ser Ser Gly Ile Val
           (Ser)                                            140

1045  GTT GCT GCC GCA GCC GGA GAA GGT TCA TCC GGA AGC ACA AGC ACA GTC GGC TAC CCT GCA AAA TAT CCT TCT
      Val Ala Ala Ala Ala Gly Glu Gly Ser Ser Gly Ser Thr Ser Thr Val Gly Tyr Pro Ala Lys Tyr Pro Ser
                             150                (Ser)             160                             170

1120  ACT ATT GCA GTA GGT GCG GTA AAC AGC AGC AAC CAA AGA GCT TCA TTC TCC AGC GCA GGT TCT GAG CTT GAT GTG
      Thr Ile Ala Val Gly Ala Val Asn Ser Ser Asn Gln Arg Ala Ser Phe Ser Ser Ala Gly Ser Glu Leu Asp Val
                             180                                190

1195  ATG GCT CCT GGC GTG TCC ATC CAA AGC ACA CTT CCT GGA GGC ACT TAC AAC GGC GCT TAT AAC GGA ACG TCC ATG GCG
      Met Ala Pro Gly Val Ser Ile Gln Ser Thr Leu Pro Gly Gly Thr Tyr Asn Gly Ala Tyr Asn Gly Thr Ser Met Ala
                             200                                210                                220

1270  ACT CCT CAC GTT GCT GCC GGA GCA GCA GCG TTA ATT CTT TCT AAG CAC CCG ACT TGG ACA AAC GCG CAA GTC CGT GAT
      Thr Pro His Val Ala Gly Ala Ala Ala Leu Ile Leu Ser Lys His Pro Thr Trp Thr Asn Ala Gln Val Arg Asp
                             230                                240

1345  CGT TTA GAA AGC ACT GCA ACA TAT CTT GGA AAC TCT TTC TAC TAT GGA AAA GGG TTA ATC AAC GTA CAA GCA GCT
      Arg Leu Glu Ser Thr Ala Thr Tyr Leu Gly Asn Ser Phe Tyr Tyr Gly Lys Gly Leu Ile Asn Val Gln Ala Ala
                             250                (Asp)260                                          270

1420  GCA CAA TAA TAG TAA AAAGAAGCAGGTTCCTCCATACCTGCTTCTTTTTATTGTCAGCATCCTGATGTTCCGGCGCATTCTTCTTCTTCTCC
      Ala Gln *** *** ***

1513  GCATGTTGAATC
```

BACILLUS STRAINS WITH REDUCED EXTRACELLULAR PROTEASE LEVELS

CROSS-REFERENCE TO RELATED APPLICATION

This application is a continuation-in-part of copending prior application Ser. No. 652,968, filed Sept. 21, 1984, now abandoned.

BACKGROUND OF THE INVENTION

The advent of recombinant DNA technology has made it possible to insert genetic information from one species into another species in such a manner that expression of the "foreign" genetic information can be effected under controlled conditions in the host organism. Thus, it has become possible to insert genes coding for a variety of useful polypeptides and proteins into common microorganisms, grow up the "transformed" microorganisms in industrial scale fermentors and produce large quantities of the polypeptides or proteins by controlled expression of the inserted genetic information. In this manner, for example, a variety of proteins having medically useful properties, such as interferons, insulin, interleukin-2, human tissue type plasminogen activator or the like, and industrially useful enzymes, such as rennin, have been produced.

Until now, most of the commercial applications of recombinant DNA technology have involved the use of *Escherichia coli* as a host microorganism. This common enteric bacteria has been thoroughly studied and is well suited for the genetic manipulations necessary to the insertion of foreign genetic information. Unfortunately, *E. coli* has a number of serious drawbacks associated with its use as a host microorganism for commercial production. The organism produces endotoxins which represent a serious threat of contamination to the desired product. The threat of contamination by endotoxins is a particularly serious problem in the production of products intended for human or animal consumption, such as medicines and hormones. Scrupulous care must be taken to assure that all traces of endotoxin have been removed from the product prior to use.

*E. coli* is not well suited for the secretion of foreign gene products from the cell. The expressed product is generally sequestered within the cell, necessitating cell lysis for recovery of the desired product. Recovering the product in this manner often requires laborious and expensive purification procedures since the desired product must be separated from numerous other intracellular proteins produced by the organism. Moreover, the accumulation of the product within the cell effectively limits the yield obtainable from a given mass of cells. Gilbert et al. (U.S. Pat. No. 4,411,994) report obtaining the excretion of insulin through the cell membrane of an *E. coli* host by fusing the insulin gene to a portion of the *E. coli* penicillinase gene containing the signal peptide coding sequence. However, the reference does not indicate that the polypeptide was secreted from the cell into the medium.

A considerable amount of effort has been expended by researchers to find expression systems (i.e., vector/host combinations) which will overcome the aforementioned drawbacks associated with the use of *E. coli* as a host for the production of heterologous (foreign) polypeptides and proteins. In particular, the art has been searching for expression systems which use non-pathogenic host organisms and which provide for expression and secretion of the desired product into the culture medium, thus simplifying recovery and increasing yields. Most of these efforts have been directed toward the construction of expression vectors containing DNA sequences which encode prokaryotic signal peptide sequences fused to the amino acid sequences of the desired polypeptides or proteins. The signal peptide is usually a sequence of about 15 to 30 residues in length, having a positively charged amino-terminal domain followed by a hydrophobic domain, which transports the attached polypeptide or protein to the cell membrane where it is deposited into the secretory pathway. By expressing the desired polypeptide or protein as a fusion with a signal peptide which is normally associated with a protein that is secreted by a prokaryotic organism, it is hoped that the prokaryotic host organism will similarly process the heterologous protein which is fused to the signal peptide. This technique has only met with limited success. For example, Palva and coworkers have reported obtaining the secretion of α-interferon from *B. subtilis* by fusing the α-interferon gene to a fragment of the *B. amyloliquefaciens* α-amylase gene containing the signal peptide coding sequence (*Gene*, 22:229-235 [1983]). The product was recoverable from the medium only in low yield.

To date, research directed toward the development of effective secretion systems has concentrated on the use of host microorganisms of the genus Bacillus, particularly Bacilli of the species *subtilis*, which are non-pathogenic and have a well-developed secretion mechanism. Bacillus species produce large quantities of extracellular protease during postexponential growth. The most abundant of these enzymes are an alkaline serine protease (subtilisin) and a neutral metalloprotease. The physiological role of subtilisin has been debated for some time.

The product of the subtilisin gene presents an important potential obstacle to the development of systems, based on Bacillus species, for the synthesis and secretion of foreign proteins encoded by recombinant genes. The inability to recover secreted foreign proteins from Bacilli in acceptable yields has led to speculation that the proteins may be synthesized at high levels only to be degraded quickly by bacterial proteases.

SUMMARY OF THE INVENTION

This invention involves the production of genetically altered strains of microorganisms of the genus Bacillus, particularly of the genus and species *Bactillus subtilis*, which are especially useful as hosts for the expression and secretion of heterologous polypeptides or proteins. The genetically altered strains of the invention have substantially reduced levels of extracellular protease production, which greatly reduces the likelihood that a secreted foreign protein will be proteolytically degraded prior to recovery.

In one embodiment of the invention, a *Bacillus subtilis* microorganism is rendered incapable of synthesizing the proteolytic enzyme subtilisin by replacing the native chromosomal DNA comprising the subtilisin gene with a DNA sequence comprising a subtilisin gene which has an inactivating DNA sequence inserted therein. Advantageously, the inactivating DNA sequence which is inserted into the subtilisin gene comprises a functional gene coding for a protein which confers a phenotypic trait, such as resistance to a selected antibiotic, which facilitates identification of the altered microorganism

BRIEF DESCRIPTION OF THE DRAWINGS

FIG. 2 is a representation of the base sequence of a 1.5 Kbp XmnI fragment (FIG. 1) carrying the apr[Bsu] gene, including the corresponding amino acid sequence of the coding segment.

DETAILED DESCRIPTION OF THE INVENTION

The genetically altered Bacillus strains of the invention are produced by replacing the chromosomal gene coding for the production of the proteolytic enzyme subtilisin with a subtilisin gene which has been inactivated. Unless otherwise qualified, the term "subtilisin", as used herein, refers to the enzyme alkaline serine protease, without regard to the species of Bacillus in which it is produced. The Bacillus strains of the invention are produced by altering the chromosomal DNA of a Bacillus using procedures analogous to those employed to effect chromosomal modifications in yeast (Scherer and Davis, *Proc. Nat. Acad. Sci. USA*, 76:4951–4955 [1979]) and in *S. typhimurium* (Gutterson and Koshland, *Proc. Nat. Acad. Sci. USA*, 80:4894–4898 [1983]). The procedures can be used to inactivate the chromosomal gene for subtilisin by insertion of additional sequences into the subtilisin gene which inactivate the gene. Advantageously, the inactivating DNA sequence comprises a functional gene coding for a protein which confers a phenotypic trait such as resistance to a specific antibiotic, so that strains carrying the desired sequence can easily be selected.

In carrying out the invention, we chose to inactivate the apr gene of *B. subtilis* by insertion of a functional cat gene coding for chloramphenicol acetyltransferase from *S. aureus*. The inserted cat gene confers chloramphenicol resistance, thus facilitating the selection of transformants.

While the methodology of the invention will be discussed hereinafter with respect to the production of genetically altered strains of the genus and species *B. subtilis*, it is to be understood that analogous procedures can be employed to produce subtilisin-deficient strains of other Bacillus species. The procedures described can be used to inactivate the subtilisin gene in a Bacillus strain which is either competent or protoplast transformable.

The process by which we produced genetically altered *Bactillus subtilis* strains of the invention involved the following general steps:

(1) Isolating a DNA fragment containing an intact apr gene from a phage lambda library of *B. subtilis* DNA sequences.

(2) Subcloning the isolated apr gene onto a shuttle vector capable of transformation and replication in both *E. coli* and *B. subtilis*.

(3) Inactivating the apr gene by insertion of a DNA fragment carrying a functional cat gene into the apr gene on the shuttle vector and isolation of a plasmid containing the inserted cat gene in the same orientation as the apr gene sequences.

(4) Transforming *B. substilis* cells with the plasmid vector containing the apr gene inactivated by the cat insert and growing the transformants under conditions in which the replication function of the plasmid is inactive.

(5) Isolating transformant *B. subtilis* strains in which the native chromosomal apr gene has been replaced by the insertionally inactivated gene.

Figure 4:
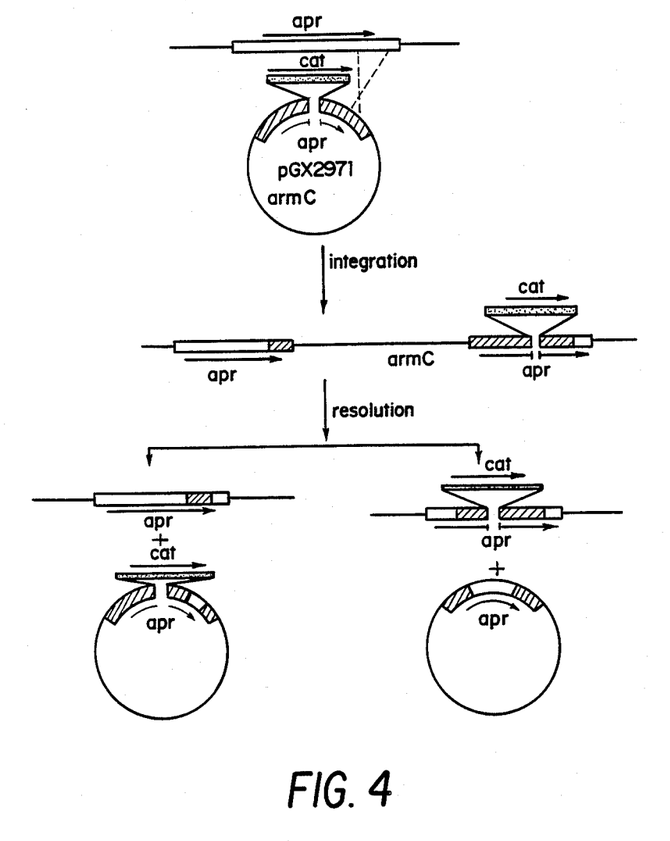
FIG. 4 is a schematic representation of the process by which the inactivated apr gene is integrated into the chromosomal DNA of some of the progeny of *B. subtilis*/pGX2971 transformants.

Following transformation, integration of the inactivated apr gene from the shuttle vector into the chromosomal DNA is believed to take place in a two-step insertion and excision process, outlined in FIG. 4. A cloned copy of the gene, inactivated in vitro and carried on the shuttle vector, is first inserted into the chromosome by homologous recombination, and the plasmid sequences are then excised in a subsequent recombination event, leaving behind, in some fraction of such progeny, the inactivated gene. The chromosomal integration step results in a tandem duplication in which one of two copies of apr is unaltered. The second step ("resolution") yields progeny which retain in the chromosome either the altered or unaltered versions of apr, respectively, in proportion determined by the length of chromosomal homology on either side of the inactivating insertion in the cloned gene. Strains containing only the altered, i.e., inactivated, apr gene can be identified by procedures described in detail below.

Using the procedures described herein, we have produced Bacillus strains which are incapable of synthesizing the enzyme subtilisin and which exhibit substantially reduced extracellular protease levels by comparison with the parent strains from which they are derived. Accordingly, they are useful as hosts for the insertion of vectors which direct the expression of polypeptides and proteins capable of being secreted into the culture medium. While subtilisin is the most abundantly produced Bacillus exoprotease, it will be readily appreciated that the procedures described herein can also be employed to inactivate other exoprotease genes in the Bacillus chromosomal DNA, thereby producing strains having even further reduced extracellular protease levels.

Since the contribution of the enzyme subtilisin to the viability of Bacilli was uncertain, it was an unpredictable finding that the genetic alteration which produced the Bacillus strains of the invention was not lethal to the organism. Moreover, the ability of the strains to produce viable heat-resistant spores was unaffected. This was unpredictable, since a relationship has been suggested between subtilisin activity and the activity of autolytic enzymes which are involved in sporulation.

In a preferred embodiment of the invention, the procedures described here were used to insert the inactivated apr gene into the chromosomal DNA of a sporulation deficient strain (Spo$^-$) of *B. subtilis* which was also Npr$^-$. The resultant strain produced very low levels of protease activity. It exhibited no metalloprotease activity and not more than 0.07 units of serine protease activity ($\Delta$ A595 per minute per A$_{600}$ equivalent unit culture supernatant, 24 hr. culture on hide powder azure substrate). The remarkable lack of "background" protease activity in this strain was unpredictable, since apr activity had never been removed from such a strain and therefore the amount of background, i.e., non-subtilisin, activity was not measurable. The Spo⁻ Npr⁻ strains carrying the inactivated apr gene are excellent candidates for use as hosts for the expression and secretion of heterologous genes.

The invention will be further understood with reference to the examples which follow. The examples are intended to be illustrative only and not to limit the scope of the invention in any way. In the examples, the abbreviation "apr[Bsu]" refers to the subtilisin (alkaline serine protease) gene of *B. subtilis* and "apr[BamP]" refers to the subtilisin (alkaline serine protease) gene of *B. amyloliquefaciens*.

Construction of the vector pGX2945

Figure 3:
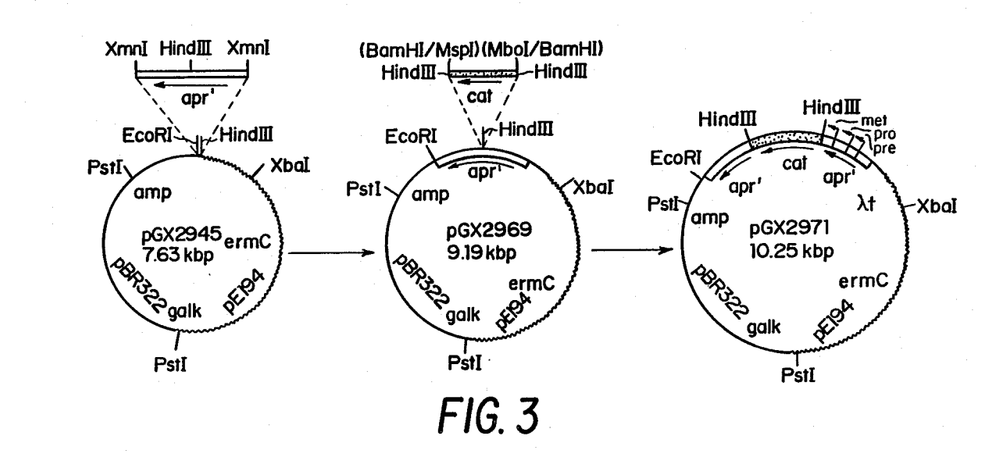
FIG. 3 is a graphic representation of the construction of plasmid pGX2971, a shuttle vector carrying an inactivated apr gene, which was used to integrate the inactivated gene into the chromosomal DNA of *B. subtilis*.

Subcloning and genetic manipulations were carried out using the shuttle vector pGX2945 (see FIG. 3). This vector was derived from pE194 (Horinouchi and Weisblum, *J. Bacteriol.*, 150:804–814 [1982]) and pGX145 (Saunders et al., *J. Bacteriol.*, 157:718–726 [1984]). For its construction pE194, linearized by digestion with AccI and blunted by brief Bal 31 nuclease treatment, was ligated to a derivative of pGX145 (containing an EcoRI-HindIII fragment bearing a superfluous fused gene) which was linearized with NruI. The fused gene sequences were then deleted from the resulting chimera by digestion with HindIII and religation. The resulting plasmid pGX2945 has pBR322 sequences between its unique EcoRI and HindIII sites (29 bp), substituted for the multisite linker sequence present there in pGX145, but is otherwise a chimera of pGX145 and pE194.

Protease Assays

Serine protease activity was determined as follows: Culture supernatant (0.2 ml) was diluted to 1 ml in a buffer containing 0.1M Tris.HCl pH 8.0, and 0.05M EDTA. Na, pH 8.0, in duplicate tubes. To one tube was added 2 mM phenylmethane sulfonyl fluoride (PMSF), and both were incubated 10 minutes at 23° C. before adding the substrate, 10 mg hide powder azure (Calbiochem). After 20–40 minutes incubation at 37° C. with shaking, remaining substrate was removed by centrifugation and the $A_{595}$ nm of the supernatant was determined after diluting with an equa volume of water. Serine protease activity is expressed as $\Delta A_{595}$ per minute per $A_{600}$ unit equivalent of culture supernatant, minus the value for the PMSF-containing blank, times 1000.

Metalloprotease activity was determined by a similar assay, except the assay buffer contained 0.1M Tris.HCl, pH 7.4, 1 mM $CaCl_2$, and 2 mM PMSF. To one of each pair of duplicate tubes was added 0.05M EDTA.Na, pH 7.4. Tubes were then treated as described above. Metalloprotease activity is expressed as $\Delta A_{595}$ per minute per $A_{600}$ nm unit equivalent of culture supernatant, minus the value for the EDTA-containing blank, times 1000.

Sporulation Assay

Cultures were grown at 37° C. in nutrient sporulation medium (Vasantha and Freese, *J. Bacteriol.*, 144:1119–1125 [1980]). After 20 or 50 hours growth, a 1 ml aliquot was incubated at 80° C. for 20 minutes, then diluted and plated on LB in 2 ml soft agar, along with an untreated control. Colonies were counted after overnight incubation at 37° C.

EXAMPLE I

Cloning and Characterization of apr[Bsu]

The *B. subtilis* subtilisin gene was isolated from a λ charon 4A library of chromosomal DNA sequence from *B. subtilis* (Ferrari et al., *J. Bacteriol.* 146:430–432 1981]). Using $^{32}$P-labeled sequences of apr[BamP] (Vasantha et al., in Ganesan and Hoch (eds.) *Genetics and Biotechnology of Bacilli*, Academic Press, N.Y. [1983]) as a probe, a plaque was identified in the phage lambda library which had cross-hybridizing sequences. This phage was found to carry a 6.6 kbp EcoRI fragment insert, illustrated in FIG. 1, which was purified by agarose gel electrophoresis and electroelution.

Figure 1:
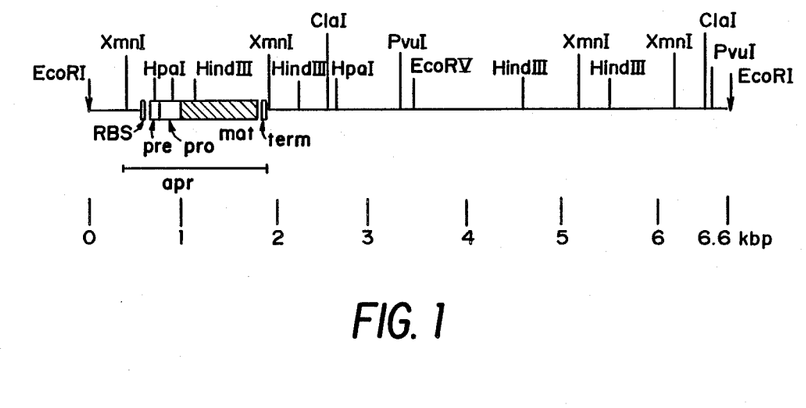
FIG. 1 is an endonuclease restriction map of a 6.6 Kilobase-pair (Kbp) DNA fragment isolated from a library of *B. subtilis* chromosomal sequences and carrying the apr gene, coding for subtilisin.

The apr[Bsu] gene was localized on this fragment by hybridization analysis with a $^{32}$P-labeled internal (PvuI) fragment of apr[BamP] as probe, and by subcloning in *B. subtilis* and analyzing the ability of subclones to produce cleared zones on plates containing 1% skim milk. This analysis located the gene on a 1.5 kb XmnI fragment (FIG. 1).

The DNA sequence and deduced amino acid sequence of this XmnI fragment is shown in FIG. 2. The sequence contains an open reading frame of 1143 nucleotides, beginning with GTG at residue 283. Translation of this sequence yields a protein 381 amino acid residues in length. Beginning at amino acid residue +1 (FIG. 2), the translated sequence is identical at 268 of 275 positions to the published amino acid sequence of subtilisin derived from *B. subtilis* var. amylosacchariticus (Kurihara et al., *J. Biol. Chem.*, 247:5619–5631 [1972]). This homologous sequence is preceded in the translated DNA sequence by 106 amino acid residues, which includes a putative secretion signal sequence and additional "pro-" sequences homologous to those reported in the apr[BamP] sequence (Wells et al., *NucAcids Res.*, 11:7911–7925 [1983]). It was concluded that the cloned sequence contained the structural gene for subtilisin (apr[Bsu]). Furthermore, the XmnI fragment carried the entire gene, including all sequences required for expression, as evidenced by the fact that *B. subtilis* clones carrying this fragment on a plasmid vector cleared enlarged zones on 1% skim milk plates.

The purified 6.6 kbp fragment was digested with XmnI, and the 1.5-kbp fragment purified by agarose gel electrophoresis and electroelution. As shown in FIG. 3, this fragment was ligated to HindIII-cut pGX2945, the ends of which had been blunted by filling-in in the presence of DNA polymerase I (Klenow fragment), and the ligation mixture was used to transform *E. coli* SK2267 to ampicillin resistance. A clone containing the correct plasmid (pGX2969) was identified, and the orientation of the insert determined by restriction analysis. Plasmid was extracted from this clone by the method of Holmes and Quigley (*Anal. Biochem.*, 114:193–197 [1981]) and used without further purification. The plasmid pGX2969 carries markers which can be selected in *E. coli* (ampicillin resistance) and in *B. subtilis* (erythromycin resistance) and can replicate as a plasmid in both species.

EXAMPLE II

Construction of Inactivation Vector

The plasmid pGX345 (Saunders et al., op. cit. 1984) contains a fragment (1.03 kbp, MspI-MboI) derived from pC194 and carrying the entire cat gene, including promoter and putative transcription terminator (Horinouchi and Weisblum, *J. Bacteriol.*, 150:815-825 1982]), in a pBR322-based vector. A HindIII site was placed upstream from this fragment by opening pGX345 at its EcoRI site, blunting by filling-in in the presence of DNA polymerase I (Klenow fragment), and reclosing with a synthetic HindIII site linker (sequence:CAAGCTTG). The cat gene was obtained from this plasmid as a 1.08 kbp HindIII fragment, which was purified by gel electrophoresis and electroelution, then inserted into the HindIII site in pGX2969 (see FIG. 3). The resulting ligation mixture was used to transform *E. coli* SK2267 to ampicillin resistance. Several transformants were identified which were also resistant to chloramphenicol. Among these, one was identified by restriction analysis in which the cat gene is oriented in the same diretion as the apr[Bsu]gene. Plasmid, identified as pGX2971, was extracted from this clone by the method of Holmes and Quigley, (op. cit.).

The HindIII site of pGX2969 into which the cat gene was inserted was located by DNA sequencing at the codon corresponding to amino acid residue 48 of mature subtilisin. This insertion separates the codon for active site residue Asp32 from codons for other active site residues His 64. and Ser 221, in addition to separating the promoter and signal peptide coding sequence from most of the mature protein coding sequence. Consequently, expression cannot yield an active subtilisin product. The fragment containing the cat gene conferred resistance to chloramphenicol in both *E. coli* and *B. subtilis*.

Plasmids bearing sequences homologous to sequences present in the chromosome of *B. subtilis*, but no replication function active in *B. subtilis*, can become integrated into the chromosome at the site of homology, (Haldenwang et al., *J. Bacteriol.*, 142:90-98 [1980]). Furthermore, pE194 (from which pGX2971 is derived) can become integrated into the chromosome, albeit at low frequency without any chromosomal homology, and be maintained there, conferring resistance to erythromycin (Hofemeister et al., *Mol. Gen. Genet.*, 189:58-68 [1983]). Such integrates can be selected by growth at 50° C. in the presence of erythromycin, since the replication function of pE194 is temperature-sensitive in *B. subtilis*, and is inactive at temperatures above 45° C. Accordingly, the plasmid pGX2971, which incorporates sequences derived from pE194, has the following properties: (a) it can be propagated in *E. coli*; (b) it can be established as an autonomous plasmid in *B. subtilis*; (c) chromosomal integrates can be selected at 50° C. in the presence of antibiotic (either erythromycin or chloramphenicol); and (d) vector sequences can be monitored via the erythromycin-resistance marker, and the inactivated apr gene can be monitored via the chloramphenicol-resistance marker.

EXAMPLE III

Transformation of *B. subtilis* and Selection of Subtilisin Deficient Strains

*B. subtilis* protoplasts were transformed by the method of Chang and Cohen (*Mol. Gen. Genet.*, 168:111-115 [1979]). Competent *B. subtilis* cells were prepared and transformed by the procedure of Saunders et al. (op. cit.). Replacement of the chromosomal apr[Bsu]gene by the insertionally inactivated version was accomplished in three strains by slightly different procedures.

(1) Competent *B. subtilis* BR151 cells were transformed. with plasmid pGX2971 DNA, isolated from *E. coli* as described above, selecting for the acquisition of chloramphenicol resistance. Among chloramphenicol-resistant transformants, 11% (11 of 100) were sensitive to erythromycin. Furthermore, all of these chloramphenicol-resistant, erythromycin-sensitive transformants retained chloramphenicol resistance at 50° C. These properties suggested that the inactivated apr gene had replaced the chromosomal copy, without establishment of pGX2971 as a plasmid. This conclusion was verified for one such transformant, designated GX4924, by Southern blot hybridization analysis (see below). *B. subtilis* strain GX4924 has been deposited at the USDA Northern Regional Research Laboratory, Peoria, Ill., with accession number B-15809.

(2) Protoplasts of a spoOA strain, 1S53, were transformed with pGX2971 DNA, selecting for chloramphenicol resistance. Among 100 transformants tested, one was sensitive to erythromycin. This transformant, designated GX4925, also retained chloramphenicol resistance at 50° C. *B. subtilis* strain GX4925 has been deposited at the USDA Northern Regional Research Laboratory, Peoria, Ill., with accession number B-15810.

(3) Protoplasts of the metalloprotease-deficient (Npr−) strain 512 were transformed with pGX2971 DNA, selecting for chloramphenicol resistance. In this case, no chloramphenicol-resistant, erythromycin-sensitive transformants (of 250 tested) were obtained—i.e., all were resistant to both drugs. Therefore, a chloramphenicol-resistant erythromycin-resistant transformant was carried through the integration-transformant resolution procedure, illustrated in FIG. 4, as follows: The plasmid-bearing transformant was grown as a patch at 50° C. on a plate containing 5 μg/ml erythromycin, then through two subsequent passages at 50° C. on a plate containing 5 μg/ml chloramphenicol, first as a patch, then as isolated colonies. Four isolated colonies from the second plate were picked to inoculate separate flasks of LB broth containing no antibiotic, which were grown to early stationary phase. Each culture was streaked on an LB plate, and 50 isolated colonies derived from each were tested for antibiotic resistance. Two of the four cultures produced only colonies resistant to chloramphenicol, but sensitive to erythromycin. Of the remaining two cultures, one produced 47 colonies resistant to both antibiotics and three resistant to neither. The other produced 40 colonies resistant to both antibiotics, six resistant to neither, three resistant to chloramphenicol, but sensitive to erythromycin, and one resistant to erythromycin but sensitive to chloramphenicol. One of the chloramphenicol-resistant, erythromycin-sensitive clones, derived from a culture which produced only such progeny, was designated GX4926. *B. subtilis* strain GX4926 has been deposited at the USDA Northern Regional Research Laboratory, Peoria, Ill., with accession number B-15811.

EXAMPLE IV

Characterization of Subtilisin-Deficient Strains

Chromosomal structure

Chromosomal DNA was prepared from each of the three strains, GX4924, GX4925, and GX4926. Separate aliquots of each preparation were digested with endonuclease XmnI, and with both EcoRI and EcoRV, respectively, and subjected to electrophoresis on a 0.8% agarose gel, along with control DNA from the parent strains. The structure of the cloned apr-containing fragment derived from the phage lambda library (FIG. 1) revealed that the apr gene is contained on a 1.52 kbp XmnI fragment, and on a 3.4 kbp EcoRI-EcoRV fragment. The 1.52 kbp XmnI fragment was isolated from the phage lambda clone, subcloned in E. coli and purified from a digest of the resulting plasmid. The purified fragment was $^{32}$P-labeled by nick translation as described by Wahl et al. (Proc. Nat. Acad. Sci. USA, 76:3683-3687 [1979]), and used as probe to analyze nitrocellulose blots of the chromosomal digests from the three transformant strains. The results, summarized in Table I, demonstrate that in all three strains the 1.1 kb cat-bearing fragment is inserted into the single chromosomal copy of the apr gene. In each case, the EcoRI-EcoRV fragment carrying apr increased in size by about 1 kb, the size of the cat fragment. Since the cat fragment contains an XmnI site, the XmnI digest revealed two hybridizing fragments for each GX4924, GX4925 and GX4926, with approximately the expected sizes. These strains therefore contain no active copy of apr[Bsu].

Protease production

Each of the strains, GX4924, GX4925 and GX4926 was grown in Penassay broth, and culture supernatants were assayed for protease activity. The results are given in Table II. All three strains showed reduced levels of extracellular serine protease activity, compared to their respective parents. None of the strains is entirely devoid of extracellular serine protease activity, however. The residual serine protease activity, which varies with the strain background, must be due to enzymes other than subtilisin.

TABLE I

Summary of Results of Southern Blot Experiments

| Source of Chromosomal DNA | Digesting Enzyme | Size (kbp) of fragments Hybridized to apr | Predicted Size |
|---|---|---|---|
| GX4924 | EcoRI + EcoRV | 4.5 | 4.48 |
|  | XmnI | 1.3 + 1.2 | 1.36 + 1.26 |
| BR151 (pE149) | EcoRI + EcoRV | 3.5 | 3.40 |
|  | XmnI | 1.5 | 1.52 |
| GX4925 | EcoRI + EcoRV | 4.5 | 4.48 |
|  | XmnI | 1.3 + 1.2 | 1.36 + 1.26 |
| 1S53 (pGX2945) | EcoRI + EcoRV | 3.5 | 3.40 |
|  | XmnI | 1.5 | 1.52 |
| GX4926 | EcoRI + EcoRV | 4.5 | 4.48 |
|  | XmnI | 1.3 + 1.2 | 1.36 + 1.26 |
| 512 | EcoRI + EcoRV | 3.5 | 3.40 |
|  | XmnI | 1.5 | 1.52 |

TABLE II

Extracellular Protease Production*

| Strain | Serine Protease 20 h | Serine Protease 50 h | Metalloprotease 20 h |
|---|---|---|---|
| GX4924 | 0.6 | 1.0 | 21 |
| BR151 (pE194) | 44 | 81 | 39 |
| GX4925 | 0.6 | 9.4 | 33 |
| 1S53 (pGX2945) | 17 | 88 | 32 |
| GX4926 | 5.9 | 39 | 0.5 |
| 512 | 28 | 92 | 0.4 |

*Protease activity accumulating in the culture supernatant during growth at 37° C. in shake-flasks on Penassay broth plus 1 mM CaCl$_2$, for the times indicated. In calculating the yield, the A$_{600}$ nm of each culture at 20 h was used to normalize both the 20 h and 50 h values. Blank values (+ PMSF) in the serine protease assays ranged from 2.6 to 5.2 at 20 h and from 6.9 to 17 at 50 h. Blank values (+ EDTA) in the metallorprotease assay ranged from 1.9 to 4.8.

EXAMPLE V

Transfer of Chromosomal DNA from GB4926 to B. subtilis BR151

It is apparent from Table II that the B. subtilis 512 host, into which the inactivated apr gene had been transferred to prepare GX4926, contained relatively high levels of background protease(s) which assayed as serine protease activity. Chromosomal DNA from GX4926, including both the inactivated apr gene and the npr mutation, was transformed into the "cleaner" background of B. subtilis BR151 to produce a strain with low levels of both serine protease activity and metalloprotease activity.

DNA was prepared from B. subtilis strain GX4926 grown in Luria broth (10 ml) to mid-log phase. Cells were separated by centrifugation and the cell pellet was resuspended in a solution of 0.4 mg./ml. lysozyme in 150 mM NaCl and 100 mM EDTA of pH 8.0. The cells were incubated for 20 minutes at 37° C. and made 1% in sodium dodecylsulfate. DNA was isolated by extracting twice with phenol:CHCl$_3$ (1:1 w/w) and precipitating the DNA from the aqueous phase with an equal volume of isopropanol. The DNA pellet was washed with 80% ethanol, dried and redissolved in 0.1 mM Tris.HCl, pH 7.8, 1 mM EDTA.

Competent B. subtilis strain BR151 cells were prepared and transformed with approximately 2-5 μg of GX4926 chromosomal DNA using the procedure of Saunders et al. (op. cit.). Chloramphenicol-resistant transformants were selected on LB agar +5 μg/ml chloramphenicol.

250 Chloramphenicol-resistant transformants were patched on LB +5 μg/ml chloramphenicol plates containing 1% casein. After overnight growth, halos (due to casein coagulation) were visualized by incubating the plates for 15 minutes at 50° C. Three of the 250 patches produced no halo, indicating lack of metalloprotease activity. One of these strains was designated GX4931 and has been deposited at the Agricultural Research Culture Collection (NRRL), Peoria, Ill. with accession number NRRL B-15961.

EXAMPLE VI

Introduction of SpoOA Mutation into GX4931

B. subtilis strain 4931, produced in Example V, was made competent by the procedure of Saunders et al. (op. cit.) and transformed with a mixture of approximately 1 μg chromosomal DNA from B. subtilis 1S53 (SpoφA677) and 1 μg of plasmid pGX2979. Selection of the desired transformants was based on "congression", that is, the tendency of competent cells to pick up several separate pieces of DNA. By screening for the presence of pGX2979, a population which was very likely to have acquired another, separate piece of DNA (the SpoφA marker on 1S53 chromosomal DNA) was obtained.

Transformants were selected on DSM +5 μg/ml erythromycin (pGX2979 contains an Em$^r$ marker). 200 Erythromycin-resistant transformants were patched on DSM plates. Sporulation on DSM is accompanied by pigment formation. After overnight growth, one of the 200 patches was white, indicating it had acquired the Spo$^-$ mutation. The rest were brown, indicating Spo$^+$.

Plasmid pGX2979 was removed from the Spo$^-$ transformants by growing through two passages on LB+5 μg/ml chloramphenicol plates at 50° C., inactivating pGX2979 replication. The resultant Spo⁻ strain, containing the inactivated apr gene and the Npr⁻ mutation, was designated GX4937. GX4937 has been deposited at the Agricultural Research Culture Collection (NRRL), Peoria, Ill., with accession no. NRRL B-15962.

EXAMPLE VII

Transformation of Spo⁻ Strain Which Is Phenotypically Npr

Protoplasts of *B. subtilis* SR22 (SpoφA12 trpC2), which is both Spo⁻ and phenotypically Npr⁻, was transformed with pGX2971, containing the inactivated apr gene, by a procedure similar to that described in Example III. All 50 chloramphenicol-resistant transformants were also erythromycin resistant. One of the Cm$^r$Em$^r$ transformants was grown through several passages on LB+5μg/ml chloramphenicol plates at 50° C. and a colony isolated which was resistant to 5 μg/ml chloramphenicol, but sensitive to 5 μg/ml erythromycin. This strain, designated GX4939, has been deposited at the Agricultural Research Culture Collection (NRRL), Peoria, Ill., with accession no. NRRL B-15963.

EXAMPLE VIII

Protease Assays of GX4931, GX4937 and GX4939

Serine protease and metalloprotease activity were assayed in GX4931, GX4937 and GX4939, with the exceptions Cultures were grown in the following medium: tryptone (33 g/L), yeast extract (20 g/L), NaCl (7.4 g/L), 3M NaOH (12 ml/L), Na$_2$HPO$_4$ (8 g/L), KH$_2$PO$_4$ (4 g/L), Casamino acids (20 g/L), glucose (10 g/L) and MnCl$_2$ (0.06 mM) at an initial pH of 7.5. 0.05 ml. culture supernatant was assayed. Units are: Change in absorbancy at 595 nm per min. per A$_{600}$ equivalent unit of culture supernatant times 1,000.

The protease activities for the three strains, as well as the parent strains, 1S53 and BR151, are given in Table III.

TABLE III

| | Protease activity* in culture supernatants | | | |
|---|---|---|---|---|
| | Metallaprotease | | Serine Protease | |
| Strain | 12 hr. | 24 hr. | 12 hr. | 24 hr. |
| GX4931 | 0.03 | 0 | 2.05 | 2.04 |
| GX4937 | −0.05 | −0.04 | 0.04 | 0.04 |
| GX4939 | 0.80 | 0 | 0.04 | 0.07 |
| 1S53 | 9.81 | 2.73 | 0.62 | 4.79 |
| BR151 | 7.33 | 0.39 | 7.26 | 8.33 |

*Substrate was hide powder azure. Metalloprotease was assayed at pH 7.4 in 2 mM PMSF. Serine protease was assayed at pH 8.0 in 50 mM EDTA. Units are ΔA595 per minute per A$_{600}$ equivalent unit culture supernatant, minus blank assayed with both EDTA and PMSF, × 1000.

As indicated in Table III, the sporulation deficient strains containing the inactivated apr gene and the npr mutation had no metalloprotease activity and not more than 0.07 units of serine protease activity for a 24 hour culture.

What is claimed is:

1. A microorganism of the genus Bacillus in which the native DNA sequence coding for the extracellular protease subtilisin has been replaced by a partially homologous DNA sequence having an alteration which renders said microorganism incapable of synthesizing subtilisin; said microorganism also containing a mutation rendering it incapable of sporulation, said mutation having the effect of decreasing the synthesis of extracellular serine proteases, other than subtilisin.

2. A microorganism as claimed in claim 1, wherein the microorganism is incapable of synthesizing the proteolytic enzyme subtilisin.

3. A microorganism as claimed in claim 1, which is of the genus and species *Bacillus subtilis*.

4. The microorganism of claim 1, wherein said mutation affecting sporulation is of the spoOA class.

5. The microorganism of claim 4, wherein said mutation affecting sporulation is due to the presence of the spoOA677 deletion allele.

6. The microorganism of claim 1, wherein said microorganism is used for the production of a protein not naturally produced by the host organism, said microorganism having been transformed with foreign DNA sequences encoding said foreign protein.

7. *Bactillus subtilis* strain GX4924.

8. *Bactillus subtilis* strain BX4925.

9. *Bactillus subtilis* strain GX4926.

10. A method of producing a Bacillus strain having reduced extracellular protease levels comprising: isolating a gene coding for the extracellular protease; inserting the gene for the extracellular protease onto a cloning vector; altering the gene on the cloning vector by inserting an inactivating DNA segment therein; transforming a microorganism of the Bacillus genus with the cloning vector capable of transformation and replication in one or more species of the genus Bacillus containing the insertionally inactivated gene coding for an extracellular protease of said microorganism, said strain containing a mutation rendering the organism incapable of sporulation; growing the transformants under conditions in which the replication function of the cloning vector is inactive; and selecting transformants in which the inactivated gene has replaced the native chromosomal DNA sequence coding for the extracellular protease.

11. A method as claimed in claim 10 wherein the inactivating DNA segment comprises a functional gene coding for a protein which confers a pheotypic trait on the transformant.

12. A method as claimed in claim 11, wherein the inactivating DNA segment comprises a functional gene coding for chloramphenicol acetyltransferase.

13. A method as claimed in claim 10, wherein the extracellular protease gene which is inactivated is a gene coding for the protease subtilisin.

14. A method as claimed in claim 10, 11, 12, or 13, wherein the Bacillus strain is of the genus and species.

15. A microorganism of the genus Bacillus which exhibits no metalloprotease activity and not more than 0.07 units of serine protease activity (ΔA595 per minute per A$_{600}$ equivalent unit culture supernatant, 24 hr. culture on hide powder azure substrate). Said microorganism containing a mutation rendering it incapable of sporulation, said mutation having the effect of decreasing the synthesis of extracellular serine proteases other than subtilisin.

16. A microorganism as claimed in claim 15, wherein the microorganism is of the genus and species *Bacillus subtilis*.

17. A microorganism as claimed in claim 15 or 16 wherein the native chromosomal DNA sequence coding for the enzyme subtilisin has been replaced by a partially homologous DNA sequence having an inactivating DNA sequence inserted therein.

18. *Bactillus subtilis*, strain GX4931.

19. *Bactillus subtilis*, strain GX4937.

20. *Bactillus subtilis*, strain GX4939.

* * * * *